US007931925B2

(12) United States Patent
Nielsen

(10) Patent No.: US 7,931,925 B2
(45) Date of Patent: *Apr. 26, 2011

(54) PROCESS FOR PRODUCING CHEESE

(75) Inventor: Per Munk Nielsen, Hillerod (DK)

(73) Assignee: Novozymes A/S, Bagsvaerd (DK)

( * ) Notice: Subject to any disclaimer, the term of this patent is extended or adjusted under 35 U.S.C. 154(b) by 73 days.

This patent is subject to a terminal disclaimer.

(21) Appl. No.: 11/867,939

(22) Filed: Oct. 5, 2007

(65) Prior Publication Data

US 2008/0032001 A1 Feb. 7, 2008

Related U.S. Application Data

(63) Continuation of application No. 10/991,206, filed on Nov. 17, 2004, now abandoned, which is a continuation of application No. 10/379,464, filed on Mar. 3, 2003, now Pat. No. 6,875,454, which is a continuation of application No. 10/087,249, filed on Mar. 1, 2002, now Pat. No. 6,551,635, which is a continuation of application No. 09/526,639, filed on Mar. 15, 2000, now Pat. No. 6,399,121.

(60) Provisional application No. 60/124,963, filed on Mar. 18, 1999.

(30) Foreign Application Priority Data

Mar. 16, 1999 (DK) .................................. 1999 00368

(51) Int. Cl.
*A23C 9/12* (2006.01)

(52) U.S. Cl. ................ 426/36; 426/34; 426/35; 426/37; 426/40; 426/582

(58) Field of Classification Search .................... 426/34, 426/35, 36, 37, 40, 580, 582; 435/134
See application file for complete search history.

(56) References Cited

U.S. PATENT DOCUMENTS

| 3,156,568 | A |   | 11/1964 | Hargrove et al. |
| 3,973,042 | A |   | 8/1976 | Kosikowski et al. |
| 4,612,197 | A |   | 9/1986 | Postner |
| 4,636,468 | A |   | 1/1987 | Arbige et al. |
| 4,861,610 | A | * | 8/1989 | Kato et al. ..................... 426/582 |
| 5,690,986 | A | * | 11/1997 | Okutomi et al. .............. 426/604 |
| 5,985,349 | A |   | 11/1999 | West et al. |
| 6,399,121 | B1 |  | 6/2002 | Nielsen |
| 6,551,635 | B2 |  | 4/2003 | Nielsen |
| 7,241,463 | B2 |  | 7/2007 | Nielsen |

FOREIGN PATENT DOCUMENTS

| EP | 0 531 104 |   | 3/1993 |
| GB | 755772 |   | 8/1956 |
| GB | 1525929 |   | 9/1978 |
| JP | 58020150 |   | 2/1983 |
| SU | 789579 |   | 12/1980 |
| SU | 938896 |   | 6/1982 |
| SU | 938896 | B * | 6/1982 |
| WO | WO 98/26057 |   | 6/1998 |
| WO | WO 9826057 A1 * | 6/1998 |
| WO | WO 00/32758 |   | 6/2000 |
| WO | WO 02/00852 |   | 1/2002 |

OTHER PUBLICATIONS

Research Disclosure No. 303014. Author Anonymous. Research Disclosure Journal No. 30314, Jul. 1989.*
Amano Enzymes News Letter, Amano Enzymes News Letter. vol. 6, pp. 4-7 (1998).
ANZFA—Australia New Zealand Good Authority. Final Risk Analysis Report—Application A402—Lipase From Genetically Modified Aspergillus Oryzae, pp. 1-36.
Arbige et al, Novel Lipase for Cheddar Cheese Flavor Development, vol. 40, No. 4, pp. 91-98 (1986).
Danisco, Flavour Division RMPS Questionnaire, vol. 2005, pp. 1-20 (2005).
Department of Health and Human Services, US Food and Drug Administration Approval No. 21, vol. 47, No. 125 (1982).
Fernandez-Garcia et al, Diary Foods, vol. 77, pp. 2139-2149 (1994).
Hoeier, Erik Declaration of Erik Hoeier (Dec. 9, 2008) pp. 1-2.
Ishihara et al, Studies on Lipase From Mucor Javanicus—Purification and Properties, vol. 388, pp. 413-422 (1975).
Kocak et al, Effect of Added Fungal Lipase on the Ripening of Kasar Cheese, vol. 51, No. 1. pp. 13-16 (1996).
Lilbaek, Journal Diary Science, vol. 89, pp. 4114-4125 (2006).
Nielsen, Per Munk, Declaration of Per Munk Nielsen (Dec. 8, 2008) p. 1.
Novozymes, Product Specification for Palatase 20000L—Valid From May 16, 2002 p. 1.
Novozymes, Enzyme Material Safety Data Sheet for Palatase 20000L, pp. 1-3 (2005).
Schmid & Verger, Lipases: Interfacial Enzymes, vol. 32. pp. 1609-1633. Review in English from Angew. Chem. Int. Ed. 37 (1998), pp. 1609-1633.
Shimizu et al, Effect of Proteolic of Milk Fat Globule Membrane on Stability of the Globules, vol. 35. No. 1, pp. 9-12 (1980).
Søe, Jørn Borsch, Declaration of Jørn Borsch Søe (Nov. 11, 2007) p. 1.
Søe, Jørn Borch, Declaration of Jørn Borch Søe (Jun. 30, 2008) pp. 1-10.
Sugimoto et al, Hydrolysis of Phosphatidyl Ethanolamine by Cell Fractions of Streptococcus Lactis, vol. 47 No. 6, pp. 1201-1206 (1983).
Van den Berg, G., Regulatory Status and Use of Lipases in Various Countries, "Chapter 5: A review of the answers on questionnaire 2192/B", Bulletin of the IDF 294.

(Continued)

*Primary Examiner* — Leslie Wong
(74) *Attorney, Agent, or Firm* — Kristin J. McNamara

(57) ABSTRACT

The present invention relates to a process for producing cheese from enzyme-treated cheese milk, and the use of the resulting produced cheese as ingredient in food products. More particularly, the present invention relates to a process for producing cheese from cheese milk treated with a enzyme selected from the group of phospholipases, in particular phospholipase $A_1$, $A_2$ and B. Also, the present invention relates to a process for stabilizing the fat emulsion of a milk composition, e.g. cream, and the use of such stabilized milk composition, e.g. for the manufacturing of UHT-cream or cream liquor.

33 Claims, No Drawings

OTHER PUBLICATIONS

Hoier et al., The Australian Journal of Dairy Technology, vol. 61, No. 2, pp. 179-182 (2006) (includes Errata Sheet).
Database Uniprot, Species Rhicomucor Miehei—NRRL 5282, Uniprot 2002-2007.
Mateos Diaz et al., Molecular Biotechnology, vol. 35, pp. 205-214 (2007).
Kurtz et el., Journal of Biological Chemistry, vol. 106, pp. 717-724 (1934).
Shipe et al., Journal of Diary Science, vol. 58, No. 8, pp. 1123-1126 (1974).
Alkanhal et al., Journal of Diary Science, Vo. 68, pp. 3162-3170 (1985).
Chrisope et al., Journal of Diary Science, vol. 59, No. 12, pp. 2024-2030 (1976).
Martin et al, Harper's Review of Biochemistry, Lange Medical Publications, 18$^{th}$ Edition, Los Altos, CA. pp. 216, 217 and 533 (1981).
Lehninger, Biochemistry, Worth Publishers, Inc., New York, p. 198. (1970).
Abstract of Japanese Patent JP 57189637 A.
Abstract of Japanese Patent JP 57189638 A.
O'Mahony et al., Journal of Diary Science, vol. 55, pp. 408-412 (1972).
J.J. Owens, Process Biochemistry, vol. 13, pp. 10, 12 and 18 (1978) XP00869553.
Picon et al., Biotechnology Letters, vol. 17, pp. 1051-1056 (1995).
Kindstedt et al, J. Diary Sci. vol. 73, pp. 867-873 (1990).
AD. Picon. "Release of Encapsulate Proteinase from dehydration-rehydration liposomes by a co-encapsulated phospholipase" XP000870477.
J.J. Owens, Process Biochemistry, p. 13.
FSTA Accession No. 82-1-03-p. 353, XP002141695.
WPI Derwent Accession No. 1983-01331K, XP002129019.
WPI Derwent Accession No. 1983-01332K, XP002129020.
"Molochnoya Promyshlenost, 1880 VSES Mauchno-Issled. 1" Maslodel'noi I Syrodel'noi promyshlennostl, Uglich, USSR, No. 11, pp. 21-25, 47, (1980).
Anon, 1989. Research Disclosure 303014, Published Jul. 1989.
Opposition filed against corresponding European patent application No. EP 1162889.
Declaration of Jøm Borsch Søe dated Mar. 17, 2007.
Harper et al., "Lipase Systems Used in the Manufacture of Italian Cheese. I. General Characteristics", Department of Dairy Technology, Institute of Nutrition and Food Technology. The Ohio State University, pp. 87-95 (1954).
Harper et al., "Lipase Systems Used in the Manufacture of Italian Cheese. II. Selective Hydrolysis", Department of Dairy Technology, The Ohio State University Agricultural Experiment Station, Wooster, pp. 556-563 (1956).
Rich et al., "The Effects of Phospholipases on Mozzarella Cheese" Session 15C, Dairy Foods, 15C-31 (2001).
Mustranta et al., "Comparison of Lipases and Phospholipases in the Hydrolysis of Phospholipids", Process Biochemistry, vol. 30, No. 5, pp. 393-401 (1995).
Telefax from Novo Nordisk to Danisco, pp. 1-3 (Jun. 8, 1998).
Palatase IVI product sheet, pp. 1-2.
Thorsen, Michael, Declaration of Michael Thorsen, pp. 1-3 (Jun. 17, 2009).
Sorensen, Jens Frisbaek, Declaration of Jens Frisbaek Sorensen, pp. 1-2 (Mar. 4, 2009).
Walstra et al, Diary Science and Technology, Second Edition, p. 43 (1999).
Sorensen, Thomas Lykke, Declaration of Thomas Lykke Soerensen & attachment : Lecitase 10L Product Sheet, pp. 1-5 (Jan. 8, 2010).
Shehata, Thesis, "Manufacture of Blue Cheese by Direct Acidification Methods," University of Wisconsin, pp. 1-99 (1966).
Jaeggi, John J. Declaration of John J. Jaeggi, Wisconsin Center for Diary Research, pp. 1-5 (Dec. 9, 2009).
Table of Contents, J. Diary Science, vol. 49, (8), pp. 1-2 (1966).
Arbige, Michale Vincent, Declaration of Michael Vincent Arbige, p. 1 (Feb. 23, 2009).
McSweeney, Paul, Declaration of Paul McSweeney, pp. 1-2 (Jun. 4, 2009).
McSweeney, Paul Curriculum Vitae PLH McSweeney, pp. 1-29.
Hoier, Eric, Chr. Hansen, Danish Diary Technical Society, pp. 1-20 (2006).
Shipe, W.F. et al., *Enzymatic Modification of Milk Favor*, Journal of Dairy Science, vol. 58, No. 8, pp. 1123-1126, 1974.
Alkanhal, H.A. et al., *Microbial Protease and Phospholipase C Stimulate Lipolysis of Washed Cream*, Journal of Dairy Science, vol. 68, No. 12, pp. 3162-3170, 1985.
Chrisope, G.L. et al., *Combined Action of Lipase and Microbila Phospholipase C on a Model Fat Globule Emulsion and Raw Milk*, Journal of Dairy Science, vol. 59, No. 12, pp. 2024-2030, 1976.
Thorsen, Michael, Declaration, pp. 1-4 (Aug. 10, 2010).
Williams, D.H. and Fleming, I., editors, Spectroscopic Methods in Organic Chemistry, 4$^{th}$ Edn., (revised) publ. McGraw-Hill, p. 158 (1989).
Validation of Analytical Procedures: Methodology, International Conference on Harmonisation of Technical Procedures (ICH), pp. 1-8 (1996).
Kelly, Alan L., Presentation at the 5th IDF Symposium of Cheese Ripening in Bern, Switzerland, available at http://www.cheese2008.ch/en/2.6.0.html, Wednesday, Session VIII, pp. 1-42 (Mar. 9-13, 2008).
Declaration of Per Munk Nielsen, Lecitase, 1 page (Nov. 5, 2010).
Food & Cosmetics—Spectral Service, 2 pages (Apr. 11, 2010).

\* cited by examiner

PROCESS FOR PRODUCING CHEESE

CROSS-REFERENCE TO RELATED APPLICATIONS

This application is a continuation of U.S. patent application Ser. No. 10/991,206 (now abandoned), filed Nov. 17, 2004, which is a divisional of U.S. patent application Ser. No. 10/379,464 (now U.S. Pat. No. 6,875,454), filed on Mar. 3, 2003, which is a continuation application of 10/087,249 (now U.S. Pat. No. 6,551,635), filed Mar. 1, 2002, which is a continuation of Ser. No. 09/526,639 (now U.S. Pat. No. 6,399,121), filed Mar. 15, 2000, which claims priority or the benefit under 35 U.S.C. 119 of U.S. provisional application No. 60/124,963, filed Mar. 18, 1999, and Danish application no. PA 1999 00368, filed Mar. 16, 1999, the contents of which are fully incorporated herein by reference.

TECHNICAL FIELD

The present invention relates to a process for producing cheese from enzyme-treated cheese milk, and the use of the resulting produced cheese as ingredient in food products. The present invention also relates to a process for stabilizing the fat in a milk composition.

BACKGROUND OF THE INVENTION

In cheese products, the state of the fat phase is important to the properties of the cheese. The fat phase is particularly important for the stabilisation of the cheese during production and ripening, but also for the final cheese to be used, eaten as such, or used in prepared ready-to-eat dishes e.g. pizza, toast or burgers.

Also, the oiling-off properties of cheese products is an important quality parameter. Oiling-off is the tendency to form free oil upon storage and melting. Excessive oiling-off is a defect most often related to heated products wherein cheese is used, e.g. pizza and related foods (cf. e.g. Kindstedt J. S; Rippe J. K. 1990, J Dairy Sci. 73: 867-873. It becomes more and more important to control/eliminate this defect, as the consumer concern about dietary fat levels increases. Free oil/fat in a product is perceived as a high fat content, and is generally undesirable.

In other food products the fat phase is often stabilised by mechanic emulsification, e.g. homogenisation. This technology is generally not applicable in cheese production as homogenisation of the cheese milk has a negative influence on the coagulation properties of the cheese milk and on the yield as well as the taste of the cheese produced therefrom.

In GB 1,525,929 it is disclosed as known to prepare stabilized oil-in-water emulsions using monoacyl glycero-phosphatide obtained by subjecting diacyl glycerophosphatide to the action of phospholipase A. GB 1,525,929 further describes use of phospholipase A treated phospholipoprotein-containing material for preparing oil-in-water emulsions, i.e. use of phospholipase treated material as an emulsion stabiliser for oil-in-water emulsions of which sauces, dressings and mayonnaise is mentioned. Cheese is not disclosed in GB 1,525,929.

So-called lecithinase activity, disclosed as phospholipase activity, has been reported for bacterial contaminants in milk, as well as the use of such milk for cheese production: "J. J Owens, Observations on lecithinases from milk contaminants, Process Biochemistry, vol. 13 no. 1, 1978, page 10-18" and "J. J Owens, Lecithinase Positive Bacteria in Milk, Process Biochemistry, vol. 13, page 13-15, 1978".

U.S. Pat. No. 4,861,610 discloses a process for preparing a cheese composition, i.e. processed cheese, for incorporation into food material where monoacyl glycero-phospholipid, fat, water and molten salt is added to cheese. The process comprises a heating treatment to dissolve the cheese (the cheese being mixed with among others mono acyl glycero phospholipid) before the addition of fat. Subsequently the cheese-composition is emulsified by a mixer. U.S. Pat. No. 4,861,610 does not disclose treatment of milk with phospholipase and manufacturing of cheese from the enzyme treated milk.

There is a need for an improved process for the manufacturing of cheese, in particular a process for improving the stability of the fat in cheese.

SUMMARY OF THE INVENTION

The invention provides a process for producing cheese, which comprises the steps of:
a) treating cheese milk or a fraction of cheese milk with a phospholipase; and
b) producing cheese from the cheese milk.
wherein step a) is conducted before and/or simultaneously with step b).

There is provided a process for improving the properties of cheeses; in particular the fat stability of cheese and cheese milk is improved by the present invention. The inventor has found that enzyme treatment of cheese milk significantly enhances the stability during a heat treatment of cheese produced from said phospholipase-treated cheese milk. By the process of the invention is also provided a method for increasing the yield in cheese production.

The invention further relates to the use of phospholipase in the manufacturing of cheese products, wherein the phospholipase treatment is conducted on the cheese milk or a fraction thereof before and/or during the production of the cheese. The invention also relates to cheeses obtainable, in particular obtained, by any of the processes described herein.

DETAILED DISCLOSURE OF THE INVENTION

The present invention relates to a process for producing cheese, which comprises the steps of:
a) treating cheese milk or a fraction of cheese milk with a phospholipase; and
b) producing cheese from the enzyme-treated cheese milk of step a),
wherein step a) is conducted before step b) and/or simultaneously with step b).

Thus, step a) and b) of the process of the invention may be conducted simultaneously, i.e. the phospholipase reacts in the cheese milk at more or less the same time as the milk coagulant forms the coagulum.

Cheese Milk and the Production of Cheese:

In the present context, the term "cheese" may be any kind of cheese and includes, e.g., natural cheese, cheese analogues and processed cheese. The cheese may be obtained by any suitable process known in the art, such as, e.g., by enzymatic coagulation of the cheese milk with rennet, or by acidic coagulation of the cheese milk with food grade acid or acid produced by lactic acid bacteria growth. In one embodiment, the cheese manufactured by the process of the invention is rennet-curd cheese. Thus, in one embodiment, the cheese is manufactured with rennet. In step b) of the process of the invention the cheese milk may be subjected to a conventional cheese-making process. Rennet is commercially available, e.g. as Naturen® (animal rennet), Chy-max® (fermentation produced chymosin), Microlant® (Microbial coagulant produced by fermentation), all from Chr-Hansen A/S, Denmark).

Processed cheese may be manufactured from natural cheese or cheese analogues by cooking and emulsifying the cheese including emulsifying salts (e.g. phosphates and citrate), and may also include spices/condiments. In one embodiment, the cheese product of the process of the invention is not processed cheese.

By cheese analogues is understood cheese-like products, in which part of the composition is non-milk constituents, such as e.g. vegetable oil. Another example for cheese analogue is cheese base. The process of the present invention is applicable in producing cheese analogues as long as the product contains fat (e.g. milk fat, such as, e.g., cream) as a part of the composition.

The cheeses produced by the process of the present invention comprise all varieties of cheese, such as, e.g. Campesino, Chester, Danbo, Drabant, Herregård, Manchego, Provolone, Saint Paulin, Soft cheese, Svecia, Taleggio, White cheese, including rennet-curd cheese produced by rennet-coagulation of the cheese curd; ripened cheeses such as Cheddar, Colby, Edam, Muenster, Gryere, Emmenthal, Camembert, Parmesan and Romano; fresh cheeses such as Mozzarella and Feta; acid coagulated cheeses such as cream cheese, Neufchatel, Quarg, Cottage Cheese and Queso Blanco; and pasta filata cheese. One embodiment relates to the production of pizza cheese by the process of the invention.

In cheese manufacturing the coagulation of the casein in milk may be performed in two ways: the so-called rennet-curd and acid-curd cheese. In cheese production these two types of curds makes up two major groups of cheese types. Fresh acid-curd cheeses refer to those varieties of cheese produced by the coagulation of milk, cream or whey via acidification or a combination of acid and heat, and which are ready for consumption once the manufacturing without ripening are completed. Fresh acid-curd cheeses generally differ from rennet-curd cheese varieties (e.g. Camberbert, Cheddar, Emmantal) where coagulation normally is induced by the action of rennet at pH values 6.4-6.6, in that coagulation normally occurs close to the isoelectric point of casein, i.e. e.g. at pH 4.6 or at higher values when elevated temperatures are used, e.g. in Ricottta pH 6.0 and 80° C. In a preferred embodiment of the invention, the cheese belongs to the class of rennet curd cheeses. In further embodiments the term cheese also includes acid curd cheese, including fresh acid-curd cheeses.

Mozzarella is a member of the so-called pasta filata, or stretched curd, cheeses which are normally distinguished by a unique plasticizing and kneading treatment of the fresh curd in hot water, which imparts the finished cheese its characteristic fibrious structure and melting and stretching properties, cf. e.g. "Mozzarella and Pizza cheese" by Paul S. Kindstedt, Cheese: Chemistry, physics and microbiology, Volume 2: Major Cheese groups, second edition, page 337-341, Chapman & Hall. Pizza cheese as used herein includes cheeses suitable for pizzas and they are usually pasta filata/stretched curd cheeses. In one embodiment, the process of the invention further comprises a heat/stretching treatment as for pasta filata cheeses, such as for the manufacturing of Mozzarella.

The cheese milk to be treated by the process of the present invention may comprise one or more of the following milk fractions: skim milk, cream, whole milk, buttermilk from production of sweet or acidified butter, whey protein concentrate, and butter or butter oil. The cheese milk to be phospholipase treated by the process of the invention may also comprise raw milk.

In further embodiments of the invention, the cheese milk to be phospholipase-treated is prepared totally or in part from dried milk fractions, such as, e.g., whole milk powder, skim milk powder, casein, caseinate, total milk protein or buttermilk powder, or any combination thereof.

The term "cheese milk", in particular in step b) of the process of the invention, is the milk-based composition from which the cheese is prepared. Thus, in the process of the invention the cheese may be produced from a milk-based composition ("the cheese milk") of which all or only a portion has been subjected to a phospholipase treatment.

The term "cheese milk" as used herein may encompass the term "fraction of the cheese milk" unless it is clear from the context that the two terms refer to different meanings. The term "fraction of the cheese milk" in the context of the invention, in particular in step a) of the process of the invention, means the fraction of the cheese milk which is subjected to the enzymatic treatment of the invention. "The fraction of the cheese milk" may comprise one or more of the milk fractions as defined herein, i.e., e.g., skim milk, cream, whole milk, buttermilk from production of sweet or acidified butter, whey protein concentrate, butter and butter oil. The butter may, e.g., be in a melted form. The fraction of the cheese milk to be treated may also comprise raw milk and it may also be prepared from dried milk fractions as already described herein. The term "fraction of the cheese milk" in the context of the present invention means one or more of the components of the cheese milk to be treated. When a fraction of the cheese milk is phospholipase treated in step a) then step a) is performed before and not during step b). After the enzymatic treatment of the fraction of the cheese milk, the fraction is combined with one or more milk fractions to make of the cheese milk from which the cheese is prepared in step b).

The enzyme treatment in step a) may be conducted on a fraction of the cheese milk or it may be conducted on the cheese milk as such. Thus, within the scope of the invention is a process for producing cheese, which comprises the steps of: step i) treating a fraction of cheese milk with a phospholipase; step ii) preparing cheese milk from the treated fraction of step i); and step iii) producing cheese from the cheese milk of step ii). It is also contemplated that in step ii) the enzyme treated cheese milk fraction of step i) may be combined with (a) non-phospholipase and/or (a) phospholipase treated cheese milk fraction(s) to provide the cheese milk from which the cheese is produced in step iii). Step i) corresponds to step a); and step iii) corresponds to step b) as used herein.

In preferred embodiments, the cheese milk or the cheese milk fraction, which is to be enzyme-treated, comprises or consists of cream. In further embodiments, the cheese milk or the fraction of the cheese milk, which is to be enzyme-treated, comprises or consists of butter. In still further embodiments, the cheese milk or the fraction of the cheese milk, which is to be enzyme-treated, comprises or consists of buttermilk. In one embodiment, the enzyme treated milk of step a) is not dried before step b). In further embodiments, the process of the invention does not include a particular step for lowering the total fat content of the cheese, such as, e.g., the process disclosed in EP 531 104 A2 which relates to a process for reducing the lipid content in food.

Milk from different species of animals may be used in the production of cheese. Thus, "milk" may be the lacteal secretion obtained by milking, e.g., cows, sheep, goats, buffaloes or camels.

The milk for production of cheese may be standardised to the desired composition by removal of a portion or of all of any of the raw milk components and/or by adding thereto additional amounts of such components. This may be done by separation of the raw milk into cream and skim milk at arrival to the dairy. Thus, the cheese milk may be prepared as done conventionally by fractioning the raw milk and recombining the fractions so as to obtain the desired final composition of the cheese milk. The separation may be made in continuous centrifuges leading to a skim milk fraction with very low fat content (i.e. e.g. <0.5%) and cream with e.g. >35% fat. The "cheese milk" may be composed by mixing cream and skim milk. In a preferred embodiment the cheese milk or the fraction of the cheese milk to be treated with phospholipase is not derived from cheese.

The cheese milk, including the cheese milk fraction, to be treated with phospholipase comprises phospholipids, such as e.g. lecithin. The cheese milk may have any total fat content which is found suitable for the cheese to be produced by the process of the invention, such as, e.g., about 25% fat (of dry matter), such as e.g. in the range 10-50% fat, of which, e.g., about 0.06% is phospholipids, such as e.g. 0.02-5% (w/w) of the total fat content is phospholipids.

Conventional steps may be taken to secure low bacterial counts in the cheese milk. It is generally preferred not to pasteurise the skim milk because heat denatured proteins in the cheese milk has a negative influence on the coagulation of the milk, and retards the ripening of the cheese. The bacterial count of the skim milk fraction may thus be lowered by other technologies, as for instance microfiltration or bactofugation. The cream may be pasteurised to get the low bacterial count in the product.

The process of the invention may further comprise the step of c) subjecting the treated cheese milk or the cheese milk fraction to a heating treatment after step a) and before step b). In one embodiment, the process of the invention comprises the steps of: step i) treating a fraction of cheese milk (such as, e.g., cream) with a phospholipase; step ii) subjecting the enzyme treated fraction of step i) to a heating treatment; step iii) combining the milk fraction of step ii) with (a) non-enzyme and/or (a) phospholipase treated milk fraction(s) to obtain the cheese milk from which the cheese is produced; and step iv) producing cheese from the cheese milk of step iii), wherein step i) corresponds to step a); and step iv) corresponds to step b) as used herein. Accordingly, in one embodiment the process of the invention, wherein the fraction of cheese milk is cream, may further comprise the step of subjecting the cream to pasteurization after step a) and before step b).

In the process of the invention the cheese milk or the fraction of the cheese milk may be subjected to a homogenization process before the production of cheese, such as e.g. in the production of Danish Blue Cheese. The homogenization may be applied before and/or after the treatment with the phospholipase. In other embodiments, however, the cheese milk in step b) is not subjected to a homogenization process before the production of cheese.

The Enzymatic Treatment:

The enzymatic treatment in the process of the invention may be conducted by dispersing the phospholipase into cheese milk or a fraction of the cheese milk, and allowing the enzyme reaction to take place at an appropriate holding-time at an appropriate temperature. The treatment with phospholipase may be carried out at conditions chosen to suit the selected enzymes according to principles well known in the art. The enzymatic treatment is a treatment in which the milk fat fraction of the cheese milk is treated with phospholipase.

The enzymatic treatment may be conducted at any suitable pH, such as e.g. in the range 2-10, such as at a pH of 4-9 or 5-7. It may be preferred to use pH of 5.5-7.0.

The process of the invention may be conducted as a phospholipase treatment of cheese milk or a fraction of the cheese milk during cold storage at 3-7° C., e.g. for at least 2 hours, e.g. in the range of 2-48 hours, or at least 5 hours, e.g. 5-24 hours. The process may also be conducted so that the phospholipase is allowed to react at coagulation conditions 30-45° C. (e.g. for at least 5 minutes, such as, e.g., for at least 10 minutes or at least 30 minutes, e.g. for 5-60 minutes) during, e.g., the cheese making process of step b). Further, the process may be conducted so that before coagulation of the cheese milk, the phospholipase is allowed to react on a milk fraction, e.g. cream, at the temperature optimum for the phospholipase, e.g. at 45-80° C., such as 47-80° C., or 50-80° C., e.g. for at least 10 minutes, such as at least 30 minutes, e.g. in the range of 10-180 minutes.

Optionally, after the enzymatic treatment the phospholipase enzyme protein is removed/reduced and/or the enzyme is inactivated.

A suitable enzyme dosage will usually be in the range of 0.01-1% (w/w) of the fat content, such as, e.g., 0.1-1.0%, particularly 0.2% (w/w) corresponding to 2000 IU per 100 g fat. One IU (International Unit) is defined as the amount of enzyme producing 1 micro mole of free fatty acid per minute under standard conditions: Egg yolk substrate (approximately 0.4% phospholipids), pH 8, 40° C., 6 mM $Ca^{++}$, Analytical method AF 280 available on request from Novo Nordisk A/S and is described in the Examples. The enzyme dosage is based on w/w fat content of the treated cheese milk such as cream illustrated in the examples. Alternatively, the enzyme dosage may be determined by the other assays as described herein.

The enzymatic treatment may be conducted batchwise, e.g. in a tank with stirring, or it may be continuous, e.g. a series of stirred tank reactors.

In one embodiment, the phospholipase is added to the cream fraction to carry out a separate phospholipase treatment of this fraction at a temperature in the range 45-80° C. In further embodiments, the phospholipase is added immediately before, or at the same time as the cheese rennet, e.g., at 32-36° C.

Enzymes to be Used in the Process of the Invention:

The enzyme used in the process of the present invention include a phospholipase, such as, phospholipase $A_1$, phospholipase $A_2$ and phospholipase B. In the process of the invention the phospholipase treatment may be provided by one or more phospholipase, such as two or more phospholipases, e.g. two phospholipases, including, without limitation, treatment with both type A and B; both type $A_1$ and $A_2$; both type $A_1$ and B; both type $A_2$ and B; or treatment with two different phospholipase of the same type. Included is also treatment with one type of phospholipase, such as $A_1$, $A_2$ or B.

Phospholipids, such as lecithin or phosphatidylcholine, consist of glycerol esterified with two fatty acids in an outer (sn-1) and the middle (sn-2) positions and esterified with phosphoric acid in the third position; the phosphoric acid, in turn, may be esterified to an amino-alcohol. Phospholipases are enzymes which participate in the hydrolysis of phospholipids. Several types of phospholipase activity can be distinguished, including phospholipases $A_1$ and $A_2$ which hydrolyze one fatty acyl group (in the sn-1 and sn-2 position, respectively) to form lysophospholipid; and lysophospholipase (or phospholipase B) which can hydrolyze the remaining fatty acyl group in lysophospholipid. Thus, the invention relates to use of enzymes that has the ability to hydrolyze one and/or both fatty acyl groups in a phospholipid.

Phospholipase $A_1$ is Defined According to Standard Enzyme EC-classification as EC 3.1.1.32.
  Official Name: Phospholipase $A_1$.
  Reaction catalyzed.
  phosphatidylcholine+$H(2)O$ <>
  2-acylglycerophosphocholine+a fatty acid anion
  Comment(s)
  has a much broader specificity than ec 3.1.1.4.
Phospholipase $A_2$ is Defined According to Standard Enzyme EC-classification as EC 3.1.1.4
  Official Name: phospholipase $A_2$.
  Alternative Name(s):phosphatidylcholine 2-acylhydrolase.
  lecithinase a; phosphatidase; or phosphatidolipase.
  Reaction catalysed:
  phosphatidylcholine+$h(2)o$<>
  1-acylglycerophosphocholine+a fatty acid anion
  comment(s): also acts on phosphatidylethanolamine, choline plasmalogen and phosphatides, removing the fatty acid attached to the 2-position.
  The term "Phospholipase A" used herein in connection with an enzyme of the invention is intended to cover an enzyme with Phospholipase $A_1$ and/or Phospholipase $A_2$ activity.
"Phospholipase B": Phospholipase B is Defined According to Standard Enzyme EC-classification as EC 3.1.1.5.
  Official Name: lysophospholipase
  Alternative Name(s):lecithinase b; lysolecithinase; phospholipase b; or plb.
  Reaction catalysed:
  2-lysophosphatidylcholine+$h(2)$
    $o$<>glycerophosphocholine+a fatty acid anion
  The term "phospholipase" used herein in connection with an enzyme of the invention is intended to cover enzymes which has enzyme activity towards phospholipids as defined herein. The term phospholipase as used herein, includes enzymes with phospholipase activity, i.e., e.g. phospholipase A ($A_1$ or $A_2$) or phospholipase B activity. The phospholipase activity may be provided by enzymes having other activities as well, such as e.g. a lipase with phospholipase activity. The phospholipase activity may e.g. be from a lipase with phospholipase side activity. In other embodiments of the invention the phospholipase enzyme activity is provided by an enzyme having essentially only phospholipase activity and wherein the phospholipase enzyme activity is not a side activity. In one embodiment of the invention, the phospholipase is not lipases having phospholipase side activity as defined in WO 98/26057.

The phospholipase may be of any origin, e.g. of animal origin (such as, e.g. mammalian), e.g. from pancreas (e.g. bovine or porcine pancreas), or snake venom or bee venom. Alternatively, the phospholipase may be of microbial origin, e.g. from filamentous fungi, yeast or bacteria, such as the genus or species *Aspergillus*, e.g. *A. niger, Dictyostelium*, e.g. *D. discoideum; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer, Sclerotinia*, e.g. *S. libertiana; Trichophyton*, e.g. *T. rubrum; Whetzelinia*, e.g. *W. sclerotiorum; Bacillus*, e.g. *B. megaterium, B. subtilis; Citrobacter*, e.g. *C. freundii; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Proteus*, e.g. *P. vulgaris; Providencia*, e.g. *P. stuartii; Salmonella*, e.g. *S. typhimurium; Serratia*, e.g. *S. liquefasciens, S. marcescens; Shigella*, e.g. *S. flexneri; Streptomyces*, e.g. *S. violeceoruber, Yersinia*, e.g. *Y. enterocolitica.* Thus, the phospholipase may be fungal, e.g. from the class Pyrenomycetes, such as the genus *Fusarium*, such as a strain of *F. culmorum, F. heterosporum, F. solani*, or a strain of *F. oxysporum*. The phospholipase may also be from a filamentous fungus strain within the genus *Aspergillus*, such as a strain of *Aspergillus awamori, Aspergillus foetidus, Aspergillus japonicus, Aspergillus niger* or *Aspergillus oryzae*. A preferred phospholipase is derived from strain of *Fusarium*, particularly *F. oxysporum*, e.g. from strain DSM 2627 as described in WO 98/26057, especially described in claim 36 and SEQ ID NO. 2 of WO 98/26057. In further embodiments, the phospholipase is a phospholipase as disclosed in PCT/DK/00664 (Novo Nordisk A/S, Denmark).

The phospholipase used in the process of the invention may be derived or obtainable from any of the sources mentioned herein. The term "derived" means in this context that the enzyme may have been isolated from an organism where it is present natively, i.e. the identity of the amino acid sequence of the enzyme are identical to a native enzyme.

The term "derived" also means that the enzymes may have been produced recombinantly in a host organism, the recombinant produced enzyme having either an identity identical to a native enzyme or having it a modified amino acid sequence, e.g. having one or more amino acids which are deleted, inserted and/or substituted, i.e. a recombinantly produced enzyme which is a mutant and/or a fragment of a native amino acid sequence. Within the meaning of a native enzyme are included natural variants. Furthermore, the term "derived" includes enzymes produced synthetically by e.g. peptide synthesis. The term "derived" also encompasses enzymes which have been modified e.g. by glycosylation, phosphorylation etc., whether in vivo or in vitro. The term "obtainable" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by e.g. peptide synthesis. With respect to recombinantly produced enzyme the terms "obtainable" and "derived" refers to the identity of the enzyme and not the identity of the host organism in which it is produced recombinantly.

Accordingly, the phospholipase may be obtained from a microorganism by use of any suitable technique. For instance, a phospholipase enzyme preparation may be obtained by fermentation of a suitable microorganism and subsequent isolation of a phospholipase preparation from the resulting fermented broth or microorganism by methods known in the art. The phospholipase may also be obtained by use of recombinant DNA techniques. Such method normally comprises cultivation of a host cell transformed with a recombinant DNA vector comprising a DNA sequence encoding the phospholipase in question and the DNA sequence being operationally linked with an appropriate expression signal such that it is capable of expressing the phospholipase in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

Suitable phospholipases are available commercially. As typical examples of the enzymes for practical use, pancreas-derived phospholipase A2 such as Lecitase® (manufactured by Novo Nordisk A/S) is preferably used.

In further embodiments, the source of the phospholipase in the process of the invention, is from expressing the enzyme by the starter organism used in the production of the cheese, such as e.g. by over-expressing the phospholipase in a lactic acid bacterium, including e.g. *lactobacillus*. Alternatively, the treatment of the cheese milk or the fraction of cheese milk is conducted by the addition of the phospholipase, optionally in combination with the phospholipase provided from the starter culture as described herein.

In a preferred embodiment, the phospholipase is not obtained from microbial milk contaminants. Accordingly, in the process of the invention, the phospholipase enzyme treatment is not provided by the enzymatic action of phospholipase expressed by a microbial milk contaminant present in the milk or the milk fraction, at least not a major portion. The microbial milk contaminants may be one or more of the group consisting of *Bacillus cereus, Bacillus cereus* var. *mycoides, Pseudomonas* sp., *Enterobacter liquifacians* (*Klebsialla cloacae*), *Alcalignes viscolactis, corynefrom rod*. In one embodiment, the phospholipase is not obtained from these contaminants. In further embodiments the phospholipase is not identical to the enzymes disclosed in "J. J Owens, Observations on lecithinases from milk contaminants, Process Biochemistry, vol. 13 no. 1, 1978, page 10-18" and "J. J Owens, Lecithinase Positive Bacteria in Milk, Process Biochemistry, vol. 13, page 13-15, 1978".

In the process of the invention, the phospholipase treatment may be performed by contacting the cheese milk and/or the cheese milk fraction with a purified phospholipase. The term "purified" as used herein covers phospholipase enzyme protein free from components from the organism from which it is derived. The term "purified" also covers phospholipase enzyme protein free from components from the native organism from which it is obtained, this is also termed "essentially pure" phospholipase and may be particularly relevant for phospholipases which are naturally occurring phospholipases and which have not been modified genetically, such as by deletion, substitution or insertion of one or more amino acid residues.

Accordingly, the phospholipase may be purified, viz. only minor amounts of other proteins being present. The expression "other proteins" relate in particular to other enzymes. The term "purified" as used herein also refers to removal of other components, particularly other proteins and most particularly other enzymes present in the cell of origin of the phospholipase. The phospholipase may be "substantially pure", i.e. free from other components from the organism in which it is produced, i.e., e.g., a host organism for recombinantly produced phospholipase. Preferably, the enzymes are at least 75% (w/w) pure, more preferably at least 80%, 85%, 90% or even at least 95% pure. In a still more preferred embodiment the phospholipase is an at least 98% pure enzyme protein preparation. In other embodiments the phospholipase is a phospholipase not naturally present in milk.

The term phospholipase includes whatever auxiliary compounds that may be necessary for the enzyme's catalytic activity, such as, e.g. an appropriate acceptor or cofactor, which may or may not be naturally present in the reaction system.

The phospholipase may be in any form suited for the use in question, such as e.g. in the form of a dry powder or granulate, a non-dusting granulate, a liquid, a stabilized liquid, or a protected enzyme. Granulates may be produced, e.g. as disclosed in U.S. Pat. Nos. 4,106,991 and 4,661,452, and may optionally be coated by methods known in the art. Liquid enzyme preparations may, for instance, be stabilized by adding stabilizers such as a sugar, a sugar alcohol or another polyol, lactic acid or another organic acid according to established methods. Protected enzymes may be prepared according to the method disclosed in EP 238,216.

By the process of the invention, the lecithin content of the cheese may be reduced by at least 5%, such as at least 10%, at least 20%, at least 30%, at least 50%, such as in the range of 5-95% compared to a similar cheese making process but without the enzymatic treatment in step a).

In cow milk the lecithin constitutes normally more than 95% of the phospholipids in milk whereas the lysolecithin is approximately 1% of the phospholipids. Although the phospholipids represent normally less than 1% of the total lipids in cow milk, they play a particularly important role, being present mainly in the milk fat globule membrane. By the process of the present invention the lecithin content in the cheese of step b) may be less than 90%, such as e.g. less than 80%, e.g. less than 60% or less than 50% of the total content of phospholipid in the cheese. In other embodiments of the invention the lysolecithin content in the cheese constitutes at least 5%, such as at least 10%, at least 20%, at least 30%, at least 50%, such as, e.g. in the range 5-99%, e.g. 5-90%, 10-90%, or 30-90% or 40-80% of the total content of phospholipids in the cheese. The lecithin or lysolecithin content may be measured by any method known by the skilled person, e.g. by HPLC.

In a preferred embodiment, it is to be understood that the relative amount of lecithin to lysolecithin in the cheese produced is provided by conversion of lecithin to lysolecithin by the treatment of the cheese milk or cheese milk fraction with phospholipase. In cheese the fat content is generally 65% (w/w), such as in the range of 10-60%.

The invention also relates to the use of phospholipase in the process of the invention. Accordingly, one embodiment relates to the use of a phospholipase in the manufacturing of a cheese product, comprising adding the phospholipase to cheese milk or a fraction of the cheese milk, and processing the cheese milk to make the cheese. Thus, within the scope of the invention is the use of a phospholipase in the manufacturing of a cheese product, wherein the phospholipase treatment is conducted on cheese milk or a fraction thereof before and/or during the production of the cheese.

The present invention further relates to use of the cheese produced by the process of the invention in pizza, ready-to-eat dishes, processed cheese or as an ingredient in other food products. Accordingly, the cheese produced according to the process of the invention may be used in further processed food products like processed cheese, pizza, burgers, toast, sauces, dressings, cheese powder or cheese flavours.

In further embodiments, the process of the invention further comprises the step of subjecting the cheese of step b) to a heating treatment, such as, e.g. in the range 150-350° C.

The invention also relates to a cheese obtainable, in particular obtained, by the process of the invention.

In a preferred embodiment, the invention relates to a process for improving the stability of the fat in cheese, the process being as described herein. In one embodiment, the cheese manufactured by the process of the invention has a lowered diffusion of fat/oil, such as, e.g., a decrease in the "oily" diameter of at least 5%, such as at least 10%, at least 20%, at least 40%, e.g. a decrease of the "oily" diameter in the range 20-800%, e.g. 20-600%; the "oily diameter" being measured as defined herein in Example 1 or 2.

In one embodiment, the invention relates to a process of the invention for increasing the yield of cheese, such as an increase in cheese fat yield and/or cheese protein yield in cheese production. Accordingly, by the present invention is provided a cheese manufacturing process leading to higher yield of the cheese and better stability of the fat phase of the cheese produced by the process of the invention. Thus, one embodiment relates to a process of the invention for improving the fat stability of cheese and/or increasing the yield in cheese production. The increase in fat-yield by the process of the invention may be at least 0.5%, such as e.g. in the range 0.5-10%, such as in the range of 0.5%-5%, measured e.g. as "fat by difference" as described in Example 3.

Further Aspects of the Invention:

The invention also provides a process for stabilizing the fat of a milk composition, which comprises treating a milk or a fraction of the milk with an enzyme selected from the group of phospholipases. The inventor has found that the emulsion stability of a milk composition can be improved by treating it with phospholipase. Thus, the invention also relates to a process for stabilizing the fat emulsion of a milk composition, which comprises treating a milk or a fraction of the milk with a phospholipase. The process may be conducted as in step a) of the process described herein.

By the present invention is also provided a method for producing improved UHT cream, in particular having improved fat stability, which process for producing UHT-cream comprises the steps of: step a) treating cream with a phospholipase; and step b) subjecting the phospholipase treated cream of step a) to UHT treatment, wherein step a) is performed before step b). The invention further relates to UHT-cream obtainable or obtained from such process of the invention. Finally, the invention relates to the use of a phospholipase in the manufacturing of UHT-cream.

By the present invention is also provided a process for producing a cream liquor, which comprises the steps of: step a) treating a milk composition (such as, e.g., cream) with a phospholipase; and step b) producing a cream liquor from the enzyme treated milk composition. The invention further relates to cream liquor obtainable or obtained from such process of the invention. Finally, the invention relates to the use of a phospholipase in the manufacturing of cream liquor.

The present invention is further illustrated in the following examples which is not to be in any way limiting to the scope of protection.

EXAMPLES

Determination of Phospholipase Activity:

The determination of the phospholipase activity may be made according to the principles described in the following. In this method is used egg yolk as a lecithin-rich substrate.
Principle: pH stat titration. Homogenized egg yolk containing phospholipids is hydrolyzed by phospholipase in the presence of calcium and sodium deoxycholate at pH 8.0 and 40° C. in a pH-stat. The released fatty acids are titrated with 0.1 N sodium hydroxide and base volume is monitored as a function of the time. One phospholipase unit is defined as the enzyme quantity which under standard conditions produces one micro-equivalent free fatty acid.
Reagents:
0.016 M Sodium deoxycholate ($C_{24}H_{39}NaO_4$), 0.32 M Calcium chloride,
0.1 N Hydrochloric acid, 0.1 N Sodium hydroxide.
Substrate: Add one egg yolk to 100 ml water and homogenize in a disperser. Filter the homogeneous substrate trough double gauze. Add 5 ml of 0.32 M calcium chloride to stabilize the filtrate.
Titrate mixture: Mix 100 ml if substrate with 50 ml of 0.016 sodium deoxycholate.

Alternatively, the following assays may be used for qualitative or quantitative determination of phospholipase activity as described in DK 99/00664 (Novo Nordisk A/S, Denmark):
"Phospholipase activity (PHLU)", "Phospholipase activity (LEU)", "Phospholipase monolayer assay", "Plate assay 1" and "Plate assay 2" or as described in WO 98/26057 (Novo Nordisk A/S): the "NEFA-C test".

Example 1

Phospholipase Treatment of Cream for Cheese Production

In this example cream was treated with phospholipase before combined with skim milk to prepare the cheese milk.
Raw Materials
Composition of the Cheese Milk:

| Skim milk | 0.1% fat | 1820 ml |
| cream | 38.0% fat | 180 ml |
| Butter milk (comprising the starter culture) | | 50 ml |
| $CaCl_2$ | | 0.4 g |

Enzymes:
1) Rennet (Acid aspartic *Rhizomucor miehei* protease—EC 3.4.23.6) dosage: 0.107 g
2) Lecitase® (pancreas-derived phospholipase $A_2$ obtainable Novo Nordisk A/S), dosage (based on fat):0.2% (w/w)
Cheese Production
Method: The cream was treated separately with phospholipase (Lecitase®, manufactured by Novo Nordisk A/S, Denmark; dosage 0.2% (based on w/w fat content)) by incubating the mixture in a 50° C. water bath for 30 minutes. The treated cream was mixed with the skim milk to a total fat content of 3.5% (w/w) of the mix, and placed in a 33-35° C. water bath. $CaCl_2$ was added to the 2 liter cheese milk, and starter culture (i.e. butter milk) was added, and the mixture was stirred for 5-10 minutes. The milk was left for 30 minutes without any stirring. Then, rennet (acid aspartic *Rhizomucor miehei* protease) was added, and the milk was stirred for 1 minute. Subsequently, the clotting point was defined (approximately 12 minutes), and the milk was standing for about 25-26 minutes before cutting.

The clotting point (clotting time) is the time passed from the addition of rennet to the first sign of flocculation, and is determined by moving a black rod in the milk i.e. the clotting point is the point when the first visible precipitation of para-casein is observed on the rod.

The actual cutting time was defined by doing a test as follows: With a clotting stick a small cut was made on the surface of the cheese, the stick was putted under the cut and moved forward, when the cheese was separated with two sharp edges, and the whey would collect in between the two edges then the cheese was ready for cutting.

The cheese was stirred gently with a whisk to break it up, and was left for two minutes. After the two minutes, the cheese was occasionally stirred during 10-15 minutes to separate the whey from the curd. The steadily appearing whey and the curd were transferred to a sieve containing a cloth. The whey drained away through the cloth for 1-2 hours. A 0.6 kg weight was placed on the top of the cheese to remove more whey, and thereafter the cheese was stored overnight at room temperature.

Result: The cheese production data (clotting time, cutting time, amount of whey, protein in whey and amount of cheese) are presented in table 1.

Melting of Cheese

Method: Before melting, the cheese was cut into pieces with a height of about 2.5 cm and diameter of about 8 cm. The cheese samples was heated in a oven at 250° C. for 8 minutes. The diameter of the cheese after heating was measured as the average of two diameters.

Result: cf. Table 1 below.

Diffusion of Fat/Oil

Method: Before the diffusion test was made, the cheese was cut into pieces with a height of about 2.5 cm and diameter of about 8 cm. The diffusion of fat/oil was measured after heating the cheese samples in an oven at 200° C. for 3 minutes. The diameter on the liquid diffused out on a filter paper—Whatman 40—after heating was measured as the average of four diameters.

Result: cf. Table 1 below.

The Measurements of Samples Obtained in Example 1 are Shown in Table 1

The trials were conducted as two set of trials, where different batches of milk/cream raw materials were used. One set is the column 1 and 2. The second set is column 3, 4 and 5.

TABLE 1

Trials with phospholipase used for treatment of cream in cheese production.

| | Trial no. | | | | |
|---|---|---|---|---|---|
| | 1*<br>Control | 2 with<br>Lecitase | 3*<br>Control | 4 with<br>Lecitase | 5 with<br>Lecitase |
| Data from Cheese production | | | | | |
| Clotting, minutes | $13^{30}$ | $14^{15}$ | $16^{20}$ | $17^{00}$ | $16^{00}$ |
| Cutting, minutes | $31^{30}$ | $31^{30}$ | $35^{50}$ | $35^{50}$ | $34^{30}$ |
| Weight of whey | 1635.5 | 1660.1 | 1625.8 | 1645.8 | 1668.7 |
| Weight of cheese | 314.75 | 296.74 | 327.44 | 322.75 | 318.77 |
| % protein in whey | 0.96 | 0.92 | 0.84 | 0.83 | 0.83 |
| g protein in whey | 15.7 | 15.3 | 13.7 | 13.7 | 13.9 |
| Result melting of cheese | | | | | |
| Average diameter after heating, cm | 8.0 | 7.5 | 8.0 | 7.3 | 7.3 |
| Result diffusion of fat/oil | | | | | |
| "Oily" diameter on filter paper after heating, cm | 6.6 | 5.8 | 6.8 | 5.4 | 5.4 |

*Trials 1 and 3, no Lecitase ® added. Trial 1* is the control for trial no. 2 and Trials 3* is the control for trial no. 4-5.

From the Result Table (cf. "melting of cheese" and "diffusion of fat/oil" shown at the bottom of Table 1) it clearly appears that cheese made with an initial phospholipase treatment of the cream improves the stability of the cheese during a heat treatment. This is seen from the measurements of the average diameter of sample after heating, which is smaller when the cream for the cheese milk has been treated with phospholipase. Further, the oily diameter on the filter paper is reduced when treating the cream with phospholipase.

The results demonstrate that it is possible to obtain a stability improvement of cheese during heat treatment with the process of the invention.

Example 2

Phospholipase Treatment of Cream to Test the Stabilising Effect on the Cream

Method: Cream (200 g) was incubated 15 minutes at 50° C. with 3 different dosages of Lecitase® 10 L, (Novo Nordisk A/S, Denmark) (dosage based on estimated fat=36%):
1. Dosage 0%
2. Dosage 0.2% (=0.0725% of the cream)
3. Dosage 1.0% (=0.36% of the cream)

After the incubation the cream was cooled to 5° C. The cream was whipped in a standardised way (Philips mixer 5 speed, the first 2 minutes run at speed 4, and speed 5 the rest of the time). 100 g whipped cream was filled into a funnel and allow to stand dripping for 1 hour at room temperature.

Samples and Results:

Sample 1 was whipped for 7 minutes and 25 seconds. About 300 ml cream. Amount of dripping after 1 hour in funnel=2.5 ml.

Sample 2 was whipped 20 minutes and no foam formation was observed. The sample became a little bit thicker, and obtained a light yellow colour.

Sample 3 was whipped for 15 minutes and no foam formation was observed. The sample became a little bit thicker and obtained a light yellow colour.

The ability to foam was destroyed by Lecitase® treatment. The foam formation in cream is based on collapse of fat globules, and formation of a continuous fat phase forming the foam. In accordance with the process of the present invention the above results show that Lecitase® treatment improves emulsification and stabilisation of the fat in the cream.

Example 3

Phospholipase Treatment of Cream for Mozzarella Cheese Production

In this example cream was treated with phospholipase before being combined with skim milk to produce the cheese milk.

Raw Materials

Composition of the Cheese Milk:

| Skim milk, pasteurised | 0.83% fat | 13.63 L |
|---|---|---|
| cream | 30% fat | 1.37 L |
| CaCl$_2$ | | 0.4 g/2 kg cream |

Starter cultures LH100 and TA061 (Lactic acid bacteria) from Rhodia Foods (Rhodia Inc, Madison, Wis., USA) 0.6 g of each.

Enzymes:
1) Rennet (Acid aspartic *Rhizomucor miehei* protease—EC 3.4.23.6) dosage w 50 KRU/g (KRU method obtainable form Novo Nordisk A/S: 0.60 g
2) Lecitase® (pancreas-derived phospholipase $A_2$ obtainable Novo Nordisk A/S), dosage (based on fat):0.2% (w/w)

Cheese Production

Method: The cream was treated separately with phospholipase (Lecitase®, manufactured by Novo Nordisk A/S, Denmark; dosage 0.2% (based on w/w fat content)) by incubating the mixture in a 50° C. water bath for 30 minutes with $CaCl_2$. The treated cream was mixed with the skim milk to a total fat content of 3.5%, and placed in 15 L cheese vat (using a cheese unit with 2×15 L vats obtainable from GEA Liquid processing, Haderslevvej 36, 6000 Kolding, Denmark). The milk was equilibrated to 34.4° C., and starter culture was added, and the mixture was gently agitated for 4-5 minutes before the rennet was added. Then, rennet (acid aspartic *Rhizomucor miehei* protease) was added, and the milk was stirred for 3 minutes. Subsequently the milk was standing for about 35 minutes before cutting The actual cutting time was defined by doing a test as follows: With a clotting stick a small cut was made on the surface of the cheese—then the stick was putted under the cut and moved forwards so as the cheese was separated with two sharp edges, and the whey would collect in between the two edges. The cutting was performed with ½ inch knifes.

The cutted curd was then heated to 41.1° C. (takes about 30 min). The cheese was then agitated gently until the curd pH reached pH 5.90, whereafter the whey was drained and piled to a 5 cm mat. The curd is cut into 1.5 inch cubes when the pH reach 5.25 and covered in cold tap water for 15 min. The curd is weighed after tap water is drained of NaCl (0.2% of the cheese milk weight) was added dry to the cubed curd in 3 portions. The curd was then stretched at 63° C. at 9 rmp by twin screw stretcher (Supreme Micro Mixing Machine obtained from Stainless Fabricating Inc., Columbus. WI, USA), where after the stretched curd is placed in 7° C. water for 30 min and 7° C. F brine (23% NaCl) for another 90 minutes.

The cheese production data (Protein in cheese, measured by Dumas Combustion Method (LECO) moisture measured by CEM Automatic Volatility Computer, model AVC-80 from CEM Corp., Matthews, N.C., 28108, and fat by difference) are collected in table 2.

Result: cf. Table 2 below.

Diffusion of Fat/Oil

Method: The diffusion of fat/oil was tested on cheese samples heated in the oven at 90° C. for 5 minutes. Before the diffusion test was made, the cheese was ground in an osterizer blender to achieve uniformity of sample. Subsequently 2.0 grams were molded into a metal ring (2 cm) and placed in the center of a Whatman # 4 filter. The oiling off was determined by difference in the areas between the ring of oil and the circle of the cheese (triplicate determinations). Result: cf. Table 2 below.

Meltability

Method: squeeze-flow rheometry, ref. Ak, M. M., and Gunasekaran. 1995. J. Texture Stud. 26: 695-711.
Parameters: 0.1 mm/sec crosshead speed on Stable Micro Systems, TA-XT2 texture analyzer. Cylindrical samples diameter 25 mm, height 15 mm) were placed in 50° C. water bath for 5 min. to equilibrate temperature.

The meltabilities of the P-lipase treated samples were only slightly lower than their respective controls.
Measurements of Samples Obtained in Examples 3 are Shown in Table 2

The trials were conducted as two set of trials, where different batches of milk/cream raw materials were used.

TABLE 2

Data for Example 3: Trials with phospholipase used for treatment of cream in cheese production.

| | Trial no. | | | |
|---|---|---|---|---|
| | 1 | 1-control | 2 | 2 control |
| Data from cheese production | | | | |
| Protein in cheese | 18.8% | 18.1% | 20.4% | 20.5% |
| Moisture | 43.1% | 45.1% | 46.3% | 46.9% |
| Fat by difference | 38.1% | 36.8% | 33.3% | 33.6% |
| Result from oiling off | | | | |
| "Oily" area on filter paper after heating, in percent of the cheese area | 57% | 176% | <10% | 61% |

*Trials 1 and 2 is with Lecitase ® added. Trial 1-control and 2-control are the corresponding trials run in parallel but without Lecitase ®. In experiment 1 the oiling of was measured after 5 days in refrigeration, and in experiment 2 the oiling of was measured after storage in refrigeration for 8 days.

From the Result Table 2 it clearly appears that mozzarella cheese made with an initial phospholipase treatment of the cream reduces the oiling off significantly, which is a key quality parameter for Mozzarella. The results demonstrate that it is possible to obtain a stability improvement of cheese during heat treatment with the process of the invention. It is furthermore seen that the Phospholipase increases the fat content in the cheese, likely caused by a reduced fat loss during processing. Thus, the initial treatment with phospholipase leads to an increase yield in cheese production.

The invention claimed is:

1. A process for producing cheese, which comprises the steps of:
    a) treating cheese milk or a fraction of cheese milk with a purified phospholipase; and
    b) producing cheese from the cheese milk or the fraction of cheese milk,
    wherein step a) is conducted before and/or during step b).

2. The process of claim 1, wherein the cheese milk or the cheese milk fraction, which is to be treated by said phospholipase, comprises one or more of cream, butter or buttermilk.

3. The process of claim 1, wherein the cheese milk or the fraction of the cheese milk, which is to be treated by said phospholipase, comprises milk fat.

4. The process of claim 1, wherein the fraction of the cheese milk is cream.

5. The process of claim 1, wherein the fraction of the cheese milk is buttermilk.

6. The process of claim 1, wherein step a) is conducted before step b).

7. The process of claim 6, wherein the milk of step a) is not dried before step b).

8. The process of claim 6, wherein the treatment in step a) is conducted on a fraction of the cheese milk.

9. The process of claim 8, wherein the fraction of cheese milk is cream, which process further comprises a step of subjecting the cream to pasteurization after step a) and before step b).

10. The process of claim 1, wherein step a) is conducted during step b).

11. The process of claim 1, wherein the treatment in step a) is conducted on the cheese milk.

12. The process of claim 1, further comprising a step of subjecting the cheese to a heating treatment.

13. The process of claim 1, wherein the cheese milk or the fraction of the cheese milk is subjected to a homogenization step before the production of cheese.

14. The process of claim 13, wherein the cheese is Danish Blue Cheese.

15. The process of claim 1, wherein the cheese is selected from the group consisting of Campesino, Chester, Danbo, Drabant, Herregård, Manchego, Provolone, Saint Paulin, Soft cheese, Svecia, Taleggio, White cheese, Cheddar, Colby, Edam, Muenster, Gryere, Emmenthal, Camembert, Parmesan, Romano, Mozzarella, Feta, cream cheese, Neufchatel, Quarg, and Queso Blanco.

16. The process of claim 1, wherein the cheese is selected from the group consisting of rennet-curd cheese produced by rennet-coagulation of the cheese curd, ripened cheeses, fresh cheeses, and acid coagulated cheeses.

17. The process of claim 1, further comprising a step of processing the cheese into a food product.

18. The process of claim 17, wherein said food product is selected from the group consisting of pizza, ready-to-eat dishes, toast, burgers, lasagna, dressing, sauces, cheese powder, cheese flavor and processed cheese.

19. The process of claim 17, wherein the cheese product is not processed cheese.

20. The process of claim 1, wherein the phospholipase is phospholipase B.

21. The process of claim 1, wherein the phospholipase is a phospholipase $A_1$ or a phospholipase $A_2$.

22. The process according to claim 1, wherein the phospholipase is an animal phospholipase or a microbial phospholipase.

23. The process of claim 22, wherein the microbial phospholipase is derived from a filamentous fungi, a yeast or a bacterium.

24. The process of claim 1, wherein the phospholipase is a pancreas-derived phospholipase.

25. The process of claim 1, further comprising a step of removing or reducing the content of the phospholipase enzyme protein after step a).

26. The process of claim 1, further comprising a step of inactivating the phospholipase after step a).

27. The process of claim 1, wherein the phospholipase treatment is conducted at pH 4-9.

28. The process of claim 1, wherein the phospholipase treatment is conducted at 3-7° C.

29. The process of claim 28, wherein the treatment in step a) is conducted before step b).

30. The process of claim 1, wherein the phospholipase treatment is conducted at 30-45° C.

31. The process of claim 30, wherein the phospholipase treatment is conducted during the cheese making process in step b).

32. The process of claim 1, wherein the phospholipase treatment is conducted at 40-80° C.

33. The process of claim 32, wherein the treatment in step a) is conducted on the fraction of the cheese milk.

* * * * *